United States Patent

Waldman et al.

[11] Patent Number: 5,158,090
[45] Date of Patent: Oct. 27, 1992

[54] METHOD AND ARRANGEMENT FOR DEPICTING STRUCTURES

[75] Inventors: Jürgen Waldman, Berlin; Manfred Krauss, Karl-Marx-Stadt; Dietrich Bilz, Berlin; Mattias Mende, Mittweida; Bernd Kriegel, Berlin, all of German Democratic Rep.

[73] Assignee: Chemnitz Technische Universitaet, Chemnitz, Fed. Rep. of Germany

[21] Appl. No.: 552,718

[22] Filed: Jul. 16, 1990

[30] Foreign Application Priority Data

Nov. 16, 1989 [DD] German Democratic Rep. ... 334606

[51] Int. Cl.$^5$ ............................................ A61B 6/03
[52] U.S. Cl. .................................. 128/664; 250/358.1
[58] Field of Search ............... 128/664, 633; 250/350, 250/341, 358.1, 349

[56] References Cited

U.S. PATENT DOCUMENTS

| 4,515,165 | 5/1985 | Carroll | 128/664 |
| 4,810,875 | 3/1989 | Wyatt | 250/227 |
| 4,907,876 | 3/1990 | Suzuki et al. | 356/41 |
| 4,910,404 | 3/1990 | Cho et al. | 250/358.1 |
| 5,039,856 | 8/1991 | Tron | 250/358.1 |

Primary Examiner—William E. Kamm
Assistant Examiner—Kevin Pontius
Attorney, Agent, or Firm—Jordan and Hamburg

[57] ABSTRACT

In a method and an arrangement for depicting structures IR light sources and receivers are disposed in one plane, and are guided as area radiators and area receivers in the x-y-z direction to the object. The area radiator radiates with a particular radiation cross section and a particular intensity. IR diodes used for radiation are triggered with a peak current preferably up to 1 amp and with a pulse frequency of preferably up to 100 kHz and the backscatter being detected. IR attenuation gradient profiles of the volume elements, determined in real time, as well as the arrangement of the area radiator-receiver sensor, enable an exact spatial assignment of the volume elements in the micrometer to centimeter range and a contrasting representation of certain structures.

4 Claims, 4 Drawing Sheets

METHOD AND ARRANGEMENT FOR DEPICTING STRUCTURES

The invention relates to a method and an arrangement for depicting structures.

FIELD OF THE INVENTION

The method and the arrangement are useful for depicting materials or micro- and macrostructures of biological tissue and organs, as well as of natural materials, technical materials and manufactured parts with the chemical and/or physical processes proceeding therein, including the volume flow of suspensions in vessels of capillary internal diameter by means of relatively low light intensities. The invention accordingly can be used in medicine and biology, as well as in nature and technology for the observation and evaluation of structures, surfaces, volumes and volume flows in natural materials and manufactured parts.

BACKGROUND OF THE INVENTION

In photoplethysmography, it is known that constant light, even that of the near infrared region, can be guided into a tissue volume and that the light emerging from the tissue can be measured or portrayed as, on the one hand, light reflected from the tissue volume. From a biophysical point of view, a constant light potential, which is modulated with respect to time and place by the biological information, for example, by the red blood dye hemoglobin, is placed in the tissue in photoplethysmography. This modulation is measured in the form of a transmission signal or a backscattered signal, the radiator and the receiver being opposite to one another or in one plane (Perinatal Medicine, 4th European Congress of Perinatal Medicine, Prague, August 1974, Georg Thieme Stuttgart Avicenum Czechoslovak Medical Press Prague, 1975, page 497; Medizintechnik 23 (1983), 76; J. Investig. Dermatol. 82 (1984) 515; Biomedizinische Technik 31 (1986), 246; Z. Klin. Med. (Berlin DDR) 43 (1988), 185, 299, 945, 1093)

A transillumination or transmission of light through the skull of a newborn with a diameter of 7.5 cm was reproduced as a "single frame image"; in addition, the transmission of the hand of an adult person was carried out at wavelengths of 840 nm and 760 nm; the penetration of the light rays was shown integrally for the status with and without hypoxia. It was also possible to differentiate a blood vessel as well as bones. The authors came to the conclusion that tissue up to several centimeters thick was sufficiently transparent for NIR radiation and permits detection of the transmitted photons, but that the spatial specificity is poor, although it is possible, in the final analysis, to resolve structures up to a depth of 1 cm (Information processing in medical imaging. Proc. of the 9th Conference, Washington, D.C., Jun. 10 to 14, 1985, Martinus Nijhoff Publish. Portrecht 1986, page 155).

The integral measurement of volumes is a common feature of these known photoplethysmographic or transillumination methods. Such an integral measurement obviously has the disadvantage that it does not measure more closely defined volumes. Measuring probes, consisting of light emitters and receivers and suitable for the measurement of microvolumes for medical investigations, are known. In these probes, the emitter and receiver are disposed immediately adjacent to one another in one plane, the light being transmitted to the measuring site by fiber-optical light guides. The measuring probe is constructed as a needle or hollow needle and, due to the provision of a diameter at the tip of 2 to 20 microns, is also suitable for detecting microstructured volume parts (German Offenlegungsschrift 3,009,901).

A disadvantage of this apparatus for the measurement of microvolume particles is the invasive or traumatic or destructive admission of the measuring probe, in the form of a hollow needle or a micropipette, to the site of the microstructure that is to be measured. If the scalp, cranium as well as the meninges must be injured with this hollow needle in order to reach the site of the measurement, for example the brain, in order thereafter to measure the brain conditionally atraumatically, then such injury is not without repercussions.

With this apparatus, light-emitting and electrically conducting substances are injected under a certain pressure into the sample that is to be investigated. For the brain, the introduction of chemical substances with this apparatus by way of injection needles or micropipettes means an intervention into the mode of functioning of this organ with the initiation of imponderable reactions. Even for the evaluation of the microcirculation of the blood, which is controlled, as is well known, in locally discrete microareas (Europ. Neurol. 20 (1981), 200), this procedure represents a possible shortcoming, which results from the measurement and possibly distorts it. Laser scanning microscopy (Chip No. 1 January (1989), which makes possible a nondestructive, repercussionless measurement of microstructures, is known. With this laser microscopy, a punctiform light source, acting over confocal system, enables surfaces, tissue, cells and microstructures within the cell even of living preparations, such as the chromosomes of an onion root, to be portrayed three dimensionally and measured at 16 different depths. The optical sections are obtained at intervals of 0.5 micrometers with a constant depth of focus. The 3-dimensional reconstruction of the individual points photographed plays a significant part. The viewing of technical materials even below the surface, for example, the alignment of enamel particles in metallic enamels, as well as the evaluation of criteria, such as the porosity, the resistance to fracture and the tear strength, are possible. If in the depth or in situ and in vivo of relative large and inhomogeneous macrostructures relatively rapid and temporal changes in microstructures of any distribution within this macrostructure are to be measured and depicted dynamically, multidimensionally, atraumatically and without repercussions in real time with relatively low radiation intensities in the milliwatt range per square centimeter per steradian, then this cannot be realized by laser microscopy. This task, namely to measure microstructures of any distribution multidimensionally in a macrostructure, can be solved partially by known magnetic resonance-tomographic methods. However, magnetic fields of several tesla, which are not without repercussions on biological structures, are required for these methods. Moreover, spectrophotometric apparatuses, which utilize light reflection or an appropriate arrangement for an noninvasive, continuous, atraumatic, in vivo application for the diagnosis of the metabolism in organs of the body, such as the brain and the heart, are known (U.S. Pat. Nos. 4,223,680, 4,281,645, 4,321,930, 4,380,240). These apparatuses apply light with two defined wavelengths to the tissue, for example in the wavelength range from of 700 to 1300 nm (in the near infrared (NIR) range).

The reflection or transmission is measured with the help of light-sensitive detectors at a relatively large distance of a few centimeters from the site of entry. As a result, the spatial measurement and evaluation is integral rather than differential.

This would have the disadvantage that only the organ as a whole or large parts of the organ, that is, relatively large volumes, can be measured or portrayed. Such a large volume element cannot be used for the finely resolving tomography and multidimensional representation, especially not if the work is to be carried out with backscattered light.

It is furthermore known that, for example, for the identification of breast cancer, the breast may penetrated by NIR radiation. Here also, however, only the transmitted radiation is measured and there is no punctiform-differential measurement (DE 31 03 609). A method is also known for the evaluation of one or more tissue parts in the brain or the female breast, known algorithms being utilized for computer tomography and the radiographic principle being employed (U.S. Pat. Nos. 4,515,165, 469,275, DD 210 202, U.S. Pat. No. 4,570,638, DE 30 19 234 C2). With this method, radiation of wavelength 700–1300 nm is passed through the tissue, the radiation being attenuated on its way. The intensity of this attenuated radiation cannot be corrected.

A method and an apparatus are disclosed in German Offenlegungsschrift 3,724,593 to keep the light, differently absorbed by the sample fluid investigated, at a predetermined amount. This is done essentially by adjusting the length of the light path in the sample. Using this method or the apparatus, for which the prerequisite essentially is the change in the path length as well as the homogeneity of the sample to be investigated, the structure of the volume flow cannot be determined dynamically, if this volume flow changes spatially and phasically in an inhomogeneous structure in the millisecond range.

There are also doubts as to whether it would be technically feasible to change the wavelength of light in an inhomogeneous body without having to change the volume that must be measured. However, inhomogeneous, different volumes do not exhibit any proportionality of the light attenuation which can be realted to the volume. For determining the blood-flow rate in large and small vessels, the Doppler flow method is known (Bibliotheca. anat. No. 18, Krager, Basel 1979, page 16; Therapiewoche 32 (1982), 5082; Int. J. Microzirkulation: Clin. exp. 5 (1986), 73; Investig. Dermatol. 82 (1984), 515). With this method, it is possible to measure the velocity of the blood corpuscle flow in the microvessels. It is a disadvantage of this method that the slow flow velocities cannot be separated and must also be measured. Here also, the Doppler flow method measures only the flow velocity of the blood components in the vessels; the actual volume flow of the red blood cells, that is, the amount of red blood cells, which infiltrates a certain cross section in a certain time, is slight relative to the flow velocity for a narrow microvessel but large relative to the flow velocity for a wide microvessel and cannot be determined with the Doppler flow method. This means that the flow velocities of the red blood cells in the vascular system are to be delineated from the volume flow through the vascular system. This volume flow affects cellular as well as noncellular constituents of the blood. In the macrovascular system, the volume flow can be measured with flow meters, if the Hagen-Poiseuille Law is taken into account. In the microcirculation region, the individual parameters no longer obey the law cited, but show deviations (Dtsch. Arch. f. Klin. Medizin 169 (1930), 212; Klin. Wschr. 7 (1928) 100). In addition, methods are known for determining the blood flow, which give information about the total flow magnitude of the volume flow, that is, of cellular and noncellular components of the blood. No distinction is made between measuring the volume flow of the red blood cells and the volume flow of the noncellular blood plasma. The blood flow is given in mL per 100 g of tissue per minute and determined nonselectively in the overall vascular system, for example, with the $^{133}$xenon isotope method (J. Neurol. Neurosurg. Psychiat. 35 (1972), 285; L'Encephale 4 (1978), 233; Brain 94 (1971), 635).

For a newer, computer-tomographic method of measuring the blood flow through the brain, namely "xenon computer tomography", nonradioactive xenon is inhaled and the blood is saturated with xenon, which in this way reaches all organs, including also the brain. The rate, at which xenon accumulates in the tissue, is a measure of the blood circulation (Chip No. 8—August 1988, pages 241-244). The additional inhalation of a nonradioactive gas is obviously a disadvantage here.

SUMMARY OF THE INVENTION

It is an object of the invention to provide a method and an arrangement for the multidimensional depiction of structures, utilizing a selective, local and volume-defined measurement of scattered light and employing IR light sources and IR light receivers, which are disposed in matrix fashion. With this method and arrangement, it shall also be possible to detect structures remote from the sensors, to depict tomographically with fine or high resolution and to determine and portray the structures punctually dynamically as volume flow. Moreover, it shall be possible to determine the volume flow selectively in the capillary vessels and with any localization within inhomogeneous structures varying spatially, temporally and qualitatively in their material composition, as well as multidimensionally in real time, the measurement of the slow flow velocity in large vessels being avoided.

Pursuant to the invention, this objective is accomplished by disposing the light sources and receivers, in one plane, and guiding them as area radiators in the z direction to the object that is to be measured or portrayed. The light sources emit an IR radiation in the NIR range with a particular radiation intensity. The IR-emitting diodes are triggered with a peak current of about 1 amp at a pulse frequency of about 100 kHz and, upon receipt of the light, and separation of the signal onto an AC channel and a DC channel, the signals are analyzed spectrally in real time. Subsequently, the signals obtained integrally and differentially for certain frequency bands are assigned to appropriate colors and displayed on a monitor as a function of the intensity, the place, the time and the wavelength. The real time spectral analysis is carried preferably for the frequency bands 0.1–4 Hz, 4–8 Hz with discretionary displacement up to 1 kHz.

The area radiator is used in x-y-z direction in the multidimensional multiplex operation in a manner such that almost overlapping or also not overlapping areas of the object to be depicted are irradiated with the area radiator. This areal irradiation leads to axial intensity focussing in the irradiated, light-scattering object and makes possible a selective illumination of the volume element which is most remote from the emitter, in the inhomogeneous object which is to be depicted and the material composition of which is changing spatially, temporally and qualitatively. This selectively illuminated volume element furthest removed from the emitter, is illuminated with radiation intensities preferably in magnitudes up to 100 mW/cm$^2$/sr of the area radiator in that the volume element, furthest removed from the emitter, is shifted intensity-stepped and intensity-proportionally into layers increasingly deeper or more remote from the emitter by the multiplex operation in the z direction and detected there differentially by multidimensional multiplex operation and as backscattered light. The volume elements can also be registered by detecting the transmitted light or by using the backscattered as well as the transmitted light to depict the structures. The irradiation of the object to be depicted is effected in pulsed operation. As a result of the axially effected intensity focussing by enlarging the area irradiated with a particular intensity per square centimeter, an increasing depth of penetration axially is achieved by the area irradiation. This is utilized by axial detection of the backscattered and/or transmitted light. The area radiator for depicting structure is also an area emitter with several IR light sources and receivers which are disposed in the x-y plane and radiate and receive in the z direction.

This area radiation sensor/receiver sensor consists of individual components, with which the structure to be depicted or the object is overlaid partially or completely in a net-like manner. The individual components are disposed in a macro-send-receive matrix and lie at different angles to one another more or less against the irregular surface of the structure to be depicted. In the case of a wide illumination overlapping the individual component, this leads to beam directions of the individual components. For this reason, one or more radiators are disposed on each component on the side away from the object to be depicted. These radiators radiate in the minus z direction and serve to position the object overlaid by the area radiator-receiver as well as to determine the position of the individual components on the object, particularly their angular position relative to one another, in a space coordinate system. Since the area radiator is moved alternatively in small-step multiplex operation in the x-y direction, in order, by so doing, to illuminate almost overlapping surfaces or to be able to illuminate selectively almost overlapping volume elements in the depth of the object to be depicted and to detect these volume elements axially without overlapping, the individual components are microstructured. For this purpose, emitters and receivers are disposed at a distance of 10-20 microns as a micromatrix on this component and as radiators of different wavelengths about the receiver. This permits the IR spectroscopic portrayal of selected materials in the NIR region or in the harmonic region of fundamental molecular oscillations with a resolution in molecular sizes or in the micrometer range. Different colors are assigned to the materials detected. On the monitor, the materials detected are shown as a function of the intensity, the place and the time, for example, time-spectroanalytically.

With the microstructured and macrostructured area sensor, the IR spectroscopic representations of volume elements are illuminated with identical intensity in situ or within inhomogeneous volume elements of the same dimensions, the material composition of which is changing temporally, spatially and qualitatively. To achieve this, the intensity of the illumination is controlled dynamically in real time by attenuation coefficients which are measured punctually and differentially and which are specific to the volume element. These attenuation gradients or volume-specific attenuation gradient profiles, which are obtained from the same volume element and differ temporally and qualitatively, are stored in a computer and used for the exact spatial assignment of the repeatedly measured volume elements in the macrostructure that is to be depicted.

The signals obtained integrally with the area radiator-receiver as well as those obtained differentially, including a contrast representation of structures within macrostructure depicted, are used for the representation.

Certain attenuation coefficients which are measured punctually and differentially and are specific to the volume element, are used for the selective determination and representation of the volume flow of a suspension in a capillary system or microvascular system within an overall vascular system consisting of large and small vessels. In this manner, portions or liquid and solid components of the suspension are determined, which infiltrate the capillary system per volume unit and time unit as integral light absorption quantities or as the difference between volume flow quantities, which change phasically and in proportion to the light absorption. This difference between particle volume flow quantities, which change with respect to the time phase and in proportion to the light absorption, is determined as the difference between the systolic proportional volume flow and the diastolic proportional volume flow of the red blood cells or as the difference of the ratios:

$$\frac{\text{cell volume flow}_{systolic}}{\text{plasma volume flow}_{systolic}} - \frac{\text{cell volume flow}_{diastolic}}{\text{plasma volume flow}_{diastolic}} = \xi$$

After the light is received, the detected signal is subjected to a real time spectral analysis and the determination or representation takes place on a monitor as a function of the intensity, the place, the time and the wavelength.

With this relationship, the particular and the nonparticular portions of a suspension, such as blood, can be determined in a biologically or naturally formed as well as in artificially or technically produced vascular systems and filters for the respective capillary system. For certain amplitudes and times $t_1$ and $t_2$, the difference between the particle volume flow quantities of the AC and DC channels, changing with the heart action or systolically/diastolically in proportion to the light absorption, can be determined as a difference ratio $$\frac{A_{ac1} - A_{ac2}}{A_{dc1} - A_{dc2}}$$

This relationship can be used to determine the self-regulation range of the microcirculation system.

The advantage of the invention is that it provides a method and an arrangement which small and large inhomogeneous structures of irregular surface can be irradiated with robust and relatively inexpensive, optoelectronic components as well as with a problem-free object application, which, for example, makes complicated, susceptible and expensive laser equipment superfluous, with relatively low light intensities of about 10 mW per square centimeter per steradian, in order to be able to determine and to represent tomographically with fine resolution, remote from the sensor, in situ and/or in vivo, multidimensionally, nondestructively and largely without repercussions, spectroanalytically as a function of time and by means of IR spectroscopy in real time their internal structures statically and dynamically, for example, the volume flow in these structures.

BRIEF FIGURE DESCRIPTION

The invention will now be explained in greater detail with reference to the associated drawings, wherein FIG. 1 schematically shows the object which is to be represented by means of the invention, as a sectional plane through the upper portion as well as its irregular surface in the lower portion of the object. The surface is overlaid in net-like fashion in the form of a matrix with IR area emitter and area receiver components. Due to the microstructure of these components, an area radiation that overlaps the components and an axial detection of the backscattered IR radiation in multidimensional multiplex operation in the x-y direction becomes possible.

DETAILED DISCLOSURE OF THE INVENTION

The invention will be explained using the brain as example. However, it is by no means limited either to this organ or to biological tissue.

Figure 1:
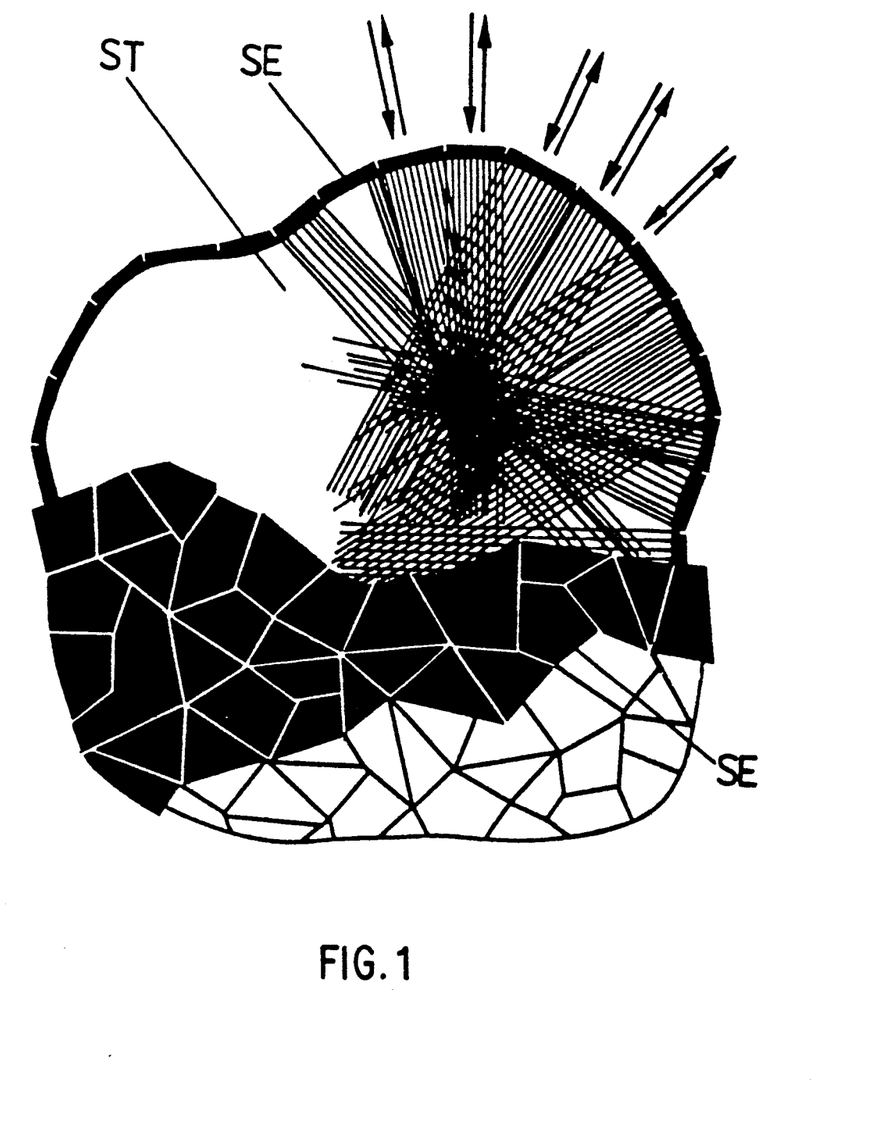
Figure 2:
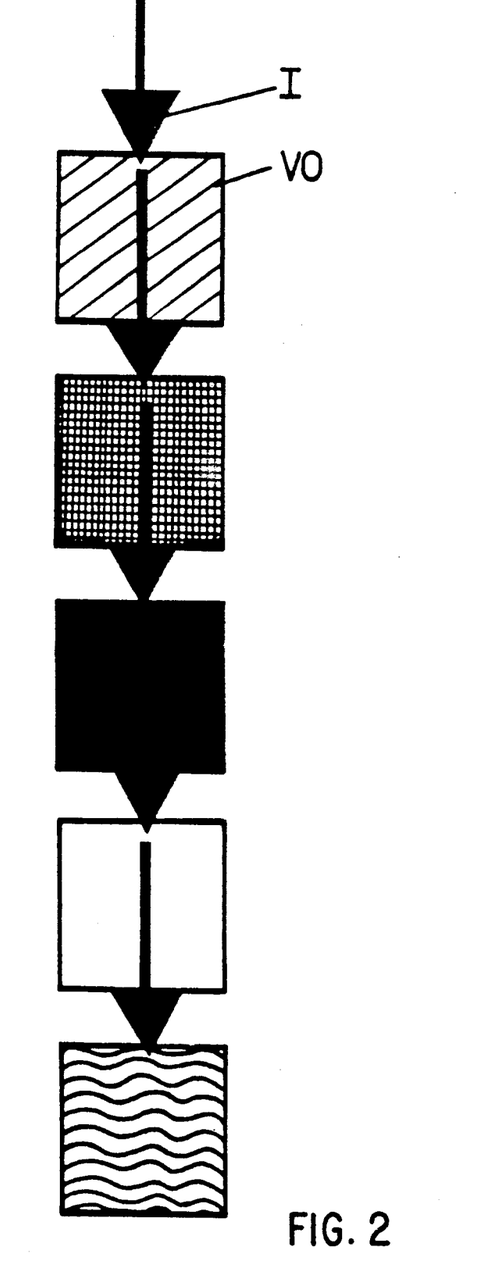
FIG. 2 diagrammatically shows the sequential selective illumination of quantitatively and qualitatively different, light attenuating microstructures or volume elements VO of the same dimensions in the z direction of an x-y-z coordinate system with the illumination intensity I in an inhomogeneous macrostructure ST, which is formed by the totality of the volume elements.

In FIGS. 1 and 2, the procedure is explained, with which an inhomogeneous, relatively large object, which is to be depicted, is irradiated by means of an area radiator, the cross section of the radiation of which can correspond to the area of the object that is to be depicted. The arrow pairs here represent sections on the sectional plane shown, for example, of the cranium, over which the area radiator is to be guided in the small multiplex steps in the x-y direction, which have been drawn here. At each multiplex step, the backscattered beam is measured axially. This measurement takes place since the radiation is carried out intensity-stepped also in the z direction in multiple operation, multidimensionally, differentially, in each case, from the volume element most remote from the emitter, since this is illuminated selectively and proportionally to the intensity by the area irradiation as a result of axial intensity focussing. Due to the real time determination of the volume element-specific NIR attenuation gradient profiles, which give the individual volume element so to say an unmistakable profile, an exact spatial assignment of the volume elements which were measured repeatedly within the macrostructure of, for example, the brain, is made possible. Due to the arrangement of radiators on the side of the components away from the object (the brain) to be depicted, and of their rays in the minus z direction, it becomes possible to determine the position of the object to be depicted, that is, of the brain or the cranium, as well as the angular position to one another of the components disposed on this irregular skull surface, so that, due to the additional arrangement, a further factor for an exact spatial assignment of the axially measured volume elements of the structure to be depicted becomes possible, even in their depth.

Since the object (brain), which is to be depicted, is to be measured and depicted by IR spectroscopy, an identical illumination intensity I must be ensured for each volume element, if the individual volume elements are to be compared with one another or depicted by NIR tomography in their intensity gradations or in their half-tone gradations. This is accomplished as a result of the fact that the NIR attenuation coefficients of each volume element measured, determined in real time, are taken into consideration when setting out to illuminate the next more remote volume element that is to be selectively illuminated.

Figure 3:
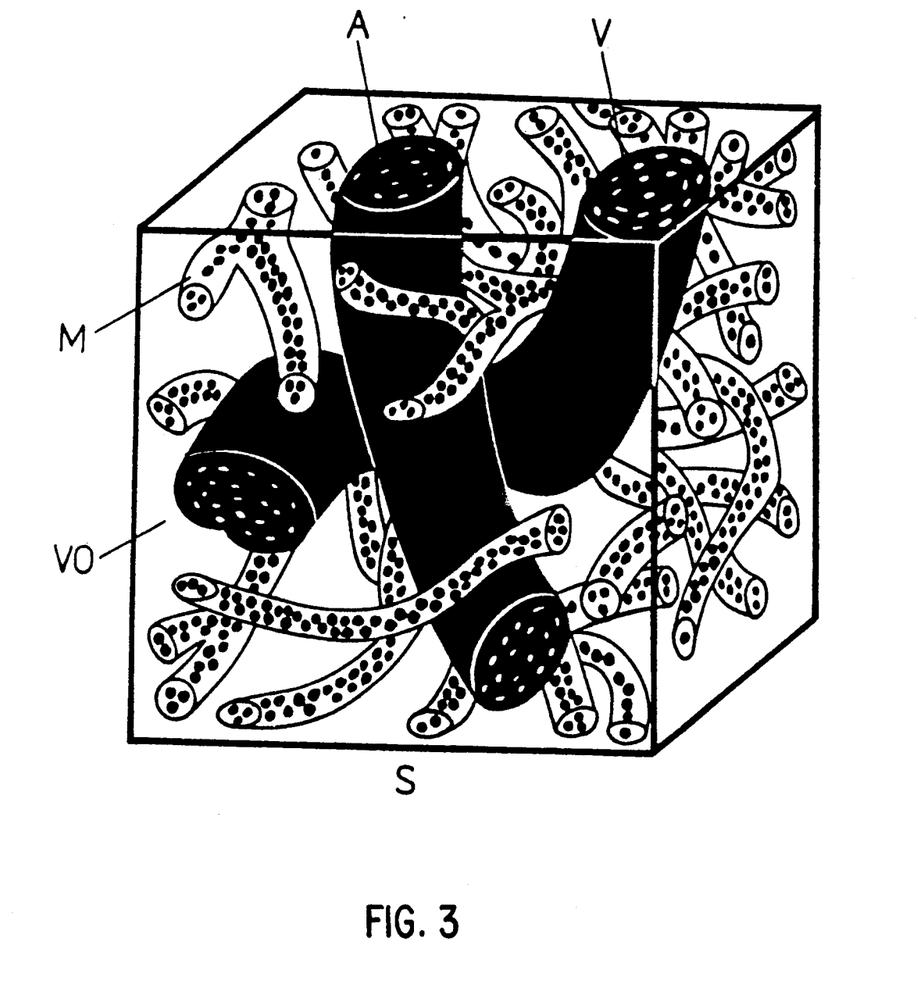
FIGS. 3 and 4 shows the same volume element VO in the systolic phase S and the diastolic phase D of the heart action with hematocrit that does not change with the time phase in the macrovessels A, V and hematocrit that does change with the time phase in the capillaries or microvessels M, in which the red blood cells flow axially and the blood plasma flows along the periphery. The proportion of red blood cells in the microvessels is higher in the systolic phase than in the diastolic phase. The number of red blood cells in the capillaries is proportional to the volume flow of the red blood cells.
Figure 4:
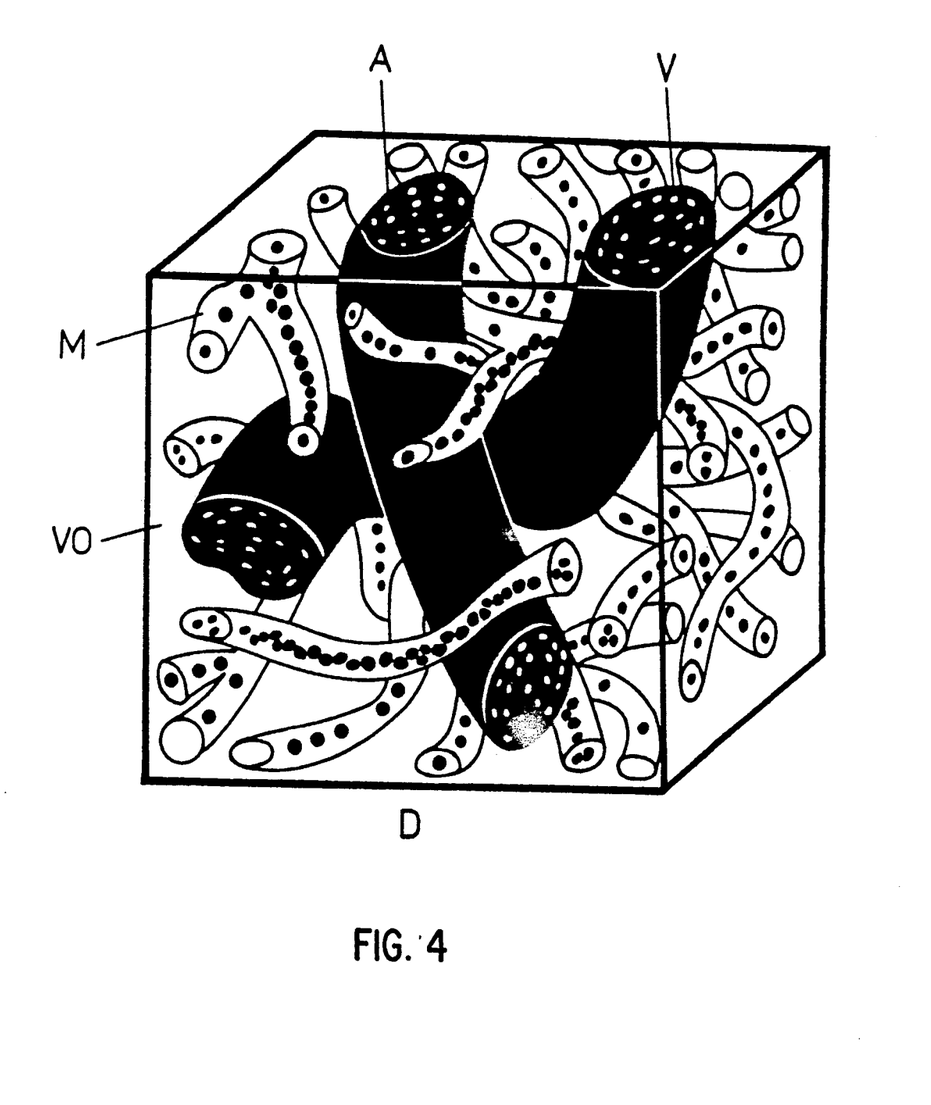

FIGS. 3 and 4 illustrate how, within an inhomogeneous structure, volume elements of the same dimensions, assuming that these volume elements are illuminated with an intensity that is identical for all the volume elements measured, show phasic changes, which can be used for the selective determination of the volume flow through the microcirculation system of this structure. In a total vascular system, comprising macrovessels as well as capillary microvessels, the particles of a suspension separate and flow axially (axially proportionally to the particle size) because of the known physical Fahraeus effect.

This volume flow is higher in the systolic phase of the heart action than in the diastolic phase. The separation, forcibly brought about by the Fahraeus effect, and the axial flow of the particular components of the blood in the capillary vascular system is to be understood as the throughput of the red blood cells through the microvascular system proportionally to the flow velocity of the red blood cells in the microvascular system. If the light absorption of the red blood cells is measured, then this absorption can be determined selectively and quantitatively, for example, at hemoglobin/oxyhemoglobin isobestic wavelengths, as the difference between the systolic and diastolic volume flows of red blood cells, that is, proportional to the time-phasic light absorption difference of the red blood cells, in the microcirculation system within the total vascular system volume-proportional to the amount of red blood cells, which permeate a volume element per unit time. This can take place selectively for different layers of a tissue, for example, the heart or the brain, or also for selectable regions and layers of industrially manufactured vascular systems and filters, in which vessels and light-scattering and absorbing media are embedded.

For example, in a mapping of 16 regions of the head, the measuring sites are selected in conformity with the ten-twenty system, which is commonly used internationally for clinical electroencephalography, since an event related mapping from the EEG to the monitor can be reproduced from the same derivation points simultaneously with the microcirculatory volume flow of the brain. The interaction between the microcirculatory volume flow and EEG can also be represented as a mapping since both EEG and the brain circulation can be analyzed spectrally as a function of time.

In contrast to EEG, the microcirculatory volume flow of layers of the brain of different depths are selectively determined. By simultaneously recording the microcirculatory volume flow and EEG, the local resolution of, for example, an event, which is possible only roughly with the EEG, can be resolved event-related in greater detail locally and the layers of different depth of the brain at 16 different regions of the head can be assigned relatively precisely in 16 intensities or half tones for a selected individual frequency of the power spectras or for several frequency bands on the monitor to the colors red, green and blue and depicted as mapping separately for each frequency band for a particular segment of time. In this manner, it becomes possible to determine dynamic processes of the volume flow as a function of the intensity, the place, the time and the wavelength. By employing a sensor-matrix with a fine resolution, dynamic NIR tomograms can be realized.

We claim:

1. A method for depicting structures, particularly while using a selective, local and volume-defined scattered light measurement with several IR diode light emitters and receivers which are disposed next to one another in an x-y plane as area radiators, said method comprising disposing light sources and receivers in one plane as area radiators and receivers to be guided in the z direction relative to an inhomogeneous object to be measured, emitting an IR radiation from the light sources in the NIR range with a particular radiation intensity, triggering the IR emitting diodes with a peak current in the milliamp to amp range at a pulse frequency in the kilohertz range and transmitting the light with an intensity modified in the x-y-z direction in multiplex operation, selectively illuminating the inhomogeneous object and the volume elements of the same dimensions, which are to be depicted therein or in situ, with an identical intensity, detecting the light and separating signals from said step of detecting into an AC channel and a DC channel, controlling the intensity in real time by punctually, differentially measured volume element-specific attenuation coefficients, obtaining these attenuation gradient coefficients from the same volume element and differing temporally, qualitatively and quantitatively, storing said coefficients in a computer and using them for assigning exact spatial assignment of the repeatedly measured volume elements as well as for selectively determining and depicting the volume flow of a suspension in a capillary vascular system within an overall vascular system of said object consisting of different vessels as integral light absorption quantities per unit volume and per unit time and determining the difference between the volume flow quantities of the capillary system, changing phasically and in proportion to the light absorption, subsequently analyzing the signals with real time spectral analysis for the frequency bands 0.1–4 Hz, 4–6 Hz and 8–12 Hz with discretionary displacement up to 1 kHz, and assigning the signals, obtained integrally and differentially for certain frequency bands to appropriate colors and depicting them as a function of intensity, location, time and wavelength.

2. A method for depicting structures, particularly while using a selective, local and volume-defined scattered light measurement with several IR diode light emitters and receivers which are disposed next to one another in an x-y plane as area radiators, said method comprising disposing light sources and receivers in one plane as area radiators and receivers to be guided in the z direction relative to an inhomogeneous object to be measured, emitting an IR radiation from the light sources in the NIR range with a particular radiation intensity, stepping or selectively changing the radiation intensity of the light sources in amounts up to 100 mW/cm$^2$/sr, triggering the IR emitting diodes with a peak current in the milliamp to amp range at a pulse frequency in the kilohertz range and transmitting the light with an intensity modified in the x-y-z direction in multiplex operation, selectively illuminating the inhomogeneous object and the volume elements of the same dimensions, which are to be depicted therein or in situ, with an identical intensity, detecting the light and separating signals from said step of detecting into an AC channel and a DC channel, controlling the intensity in real time by punctually, differentially measured volume element-specific attenuation coefficients, obtaining these attenuation gradient coefficients from the same volume element and differing temporally, qualitatively and quantitatively, storing said coefficients in a computer and using them for assigning exact spatial assignment of the repeatedly measured volume elements as well as for selectively determining and depicting the volume flow of a suspension in a capillary vascular system within an overall vascular system of said object consisting of different vessels as integral light absorption quantities per unit volume and per unit time and determining the difference between the volume flow quantities of the capillary system, changing phasically and in proportion to the light absorption, subsequently analyzing the signals with real time spectral analysis, and assigning the signals, obtained integrally and differentially for certain frequency bands to appropriate colors and depicting them as a function of intensity, location, time and wavelength.

3. A method for depicting structures, particularly while using a selective, local and volume-defined scattered light measurement with several IR diode light emitters and receivers which are disposed next to one another in an x-y plane as area radiators, said method comprising disposing light sources and receivers in one plane as area radiators and receivers to be guided in the z direction relative to an inhomogeneous object to be measured, emitting an IR radiation from the light sources in the NIR range with a particular radiation intensity, triggering the IR emitting diodes with a peak current in the milliamp to amp range at a pulse frequency in the kilohertz range and transmitting the light with an intensity modified in the x-y-z direction in multiplex operation, selectively illuminating the inhomogeneous object and the volume elements of the same dimensions, which are to be depicted therein or in situ, with an identical intensity, detecting the light and separating signals from said step of detecting into an AC channel and a DC channel, controlling the intensity in real time by punctually, differentially measured volume element-specific attenuation coefficients, obtaining these attenuation gradient coefficients from the same volume element and differing temporally, qualitatively and quantitatively, storing said coefficients in a computer and using them for assigning exact spatial assignment of the repeatedly measured volume elements as well as for selectively determining and depicting the volume flow of a suspension in a capillary vascular system within an overall vascular system of said object consisting of different vessels as integral light absorption quantities per unit volume and per unit time and determining the difference between the volume flow quantities of the capillary system, changing phasically and in proportion to the light absorption, subsequently analyzing the signals with real time spectral analysis, assigning the signals, obtained integrally and differentially for certain frequency bands to appropriate colors and depicting them as a function of intensity, location, time and wavelength, and using certain volume element-specific attenuation gradients for the contrasting representation of certain structures.

4. A method for depicting structures, particularly while using a selective, local and volume-defined scattered light measurement with several IR diode light emitters and receivers which are disposed next to one another in an x-y plane as area radiators, said method comprising disposing light sources and receivers in one plane as area radiators and receivers to be guided in the z direction relative to an inhomogeneous object to be measured, emitting an IR radiation from the light sources in the NIR range with a particular radiation intensity, triggering the IR emitting diodes with a peak current in the milliamp to amp range at a pulse frequency in the kilohertz range and transmitting the light with an intensity modified in the x-y-z direction in multiplex operation, selectively illuminating the inhomogeneous object and the volume elements of the same dimensions, which are to be depicted therein or in situ, with an identical intensity, detecting the light and separating signals from said step of detecting into an AC channel and a DC channel, controlling the intensity in real time by punctually, differentially measured volume element-specific attenuation coefficients, obtaining these attenuation gradient coefficients from the same volume element and differing temporally, qualitatively and quantitatively, storing said coefficients in a computer and using them for assigning exact spatial assignment of the repeatedly measured volume elements as well as for selectively determining and depicting the volume flow of a suspension in a capillary vascular system within an overall vascular system of said object consisting of different vessels as integral light absorption quantities per unit volume and per unit time and determining the difference between the volume flow quantities of the capillary system, changing phasically and in proportion to the light absorption, subsequently analyzing the signals with real time spectral analysis, and assigning the signals, obtained integrally and differentially for certain frequency bands to appropriate colors and depicting them as a function of intensity, location, time and wavelength, and using the attenuation gradients, obtained by IR spectroscopy to depict certain structures.

* * * * *